(12) United States Patent
Hu et al.

(10) Patent No.: US 9,730,646 B2
(45) Date of Patent: Aug. 15, 2017

(54) ASSAY DEVICE FOR TESTING AN ANALYTE IN SAMPLES

(75) Inventors: Lin Hu, Hangzhou (CN); Haipeng Hu, Hangzhou (CN)

(73) Assignee: Abon Biopharm (Hangzhou) Co., Ltd, Hangzhou (CN)

(*) Notice: Subject to any disclaimer, the term of this patent is extended or adjusted under 35 U.S.C. 154(b) by 780 days.

(21) Appl. No.: 14/110,206

(22) PCT Filed: Mar. 30, 2012

(86) PCT No.: PCT/CN2012/073292
§ 371 (c)(1),
(2), (4) Date: Oct. 7, 2013

(87) PCT Pub. No.: WO2012/146116
PCT Pub. Date: Nov. 1, 2012

(65) Prior Publication Data
US 2014/0046215 A1    Feb. 13, 2014

(30) Foreign Application Priority Data

Apr. 29, 2011    (CN) .......................... 2011 1 0115654

(51) Int. Cl.
*A61B 5/00* (2006.01)
*A61B 10/00* (2006.01)
*A61B 5/145* (2006.01)
*B01L 3/00* (2006.01)

(52) U.S. Cl.
CPC ........ *A61B 5/7405* (2013.01); *A61B 5/14507* (2013.01); *A61B 10/007* (2013.01); *A61B 10/0051* (2013.01); *B01L 3/50825* (2013.01); *B01L 3/5023* (2013.01); *B01L 2200/143* (2013.01); *B01L 2300/042* (2013.01); *B01L 2300/0663* (2013.01); *B01L 2300/0832* (2013.01); *B01L 2400/0433* (2013.01)

(58) Field of Classification Search
CPC B65D 41/34; B65D 41/3404; B65D 41/3423; B65D 41/3442
See application file for complete search history.

(56) References Cited

U.S. PATENT DOCUMENTS 5,186,344 A    2/1993    Cook

FOREIGN PATENT DOCUMENTS

| CN | 1665724 A | 9/2005 |
|---|---|---|
| CN | 101181942 A | 5/2008 |
| CN | 201572649 U | 9/2010 |
| CN | 102072950 A | 5/2011 |
| CN | 202221428 U | 5/2012 |
| EP | 2 080 711 A1 | 7/2009 |
| WO | WO 2011/060623 * 5/2011 ............. G01N 33/50 |

* cited by examiner

*Primary Examiner* — Michael C Stout
*Assistant Examiner* — Nicholas E Kolderman
(74) *Attorney, Agent, or Firm* — DLA Piper LLP (US)

(57) ABSTRACT

This invention provides an assay device for testing an analyte in samples, comprising a chamber with an opening for collecting samples, a test element, and a sound indication structure. The indication structure creates sound by vibrating after the structure deforms and would move back to the original position. The assay device is easy to operate for non-professionals.

9 Claims, 10 Drawing Sheets

ASSAY DEVICE FOR TESTING AN ANALYTE IN SAMPLES

CROSS REFERENCE TO RELATED APPLIICATIONS

This application is a 35 USC§371 National Stage application of International Application No. PCT/CN2012/073292 filed Mar. 30, 2012, now pending; which claims the benefit under 35 USC §119(a) of China Patent Application No. 201110116564.5 filed Apr. 29, 2011. The disclosure of each of the prior applications is considered part of and is incorporated by reference in the disclosure of this application.

FIELD OF THE INVENTION

This invention relates to an assay device for testing if an analyte is present in liquid samples

BACKGROUND OF THE INVENTION

It is a common practice of testing body fluid in the medical and healthcare field. The diagnostic test is applied more and more widely by workshops, government agencies, sport teams and other organizations to ensure safety at public places and compliance with laws, regulation and rules.

It is a very popular method to use an assay device to collect liquid samples such as urine to determine if a certain analyte (eg: drug and/or metabolite thereof, or some markers associated with diseases) is present in the sample. When such assay devices are used, samples are generally required to put into sample containers and a technician related has to dip a part of test strip into the collected sample and read the test result after taking out the test strip. Under such circumstances, the technician may contact the sample, which probably endangers his/her health or contaminates the sample. Therefore the sample container shall be sealed with a cover body before operation to avoid such risk. At present, a plurality of airtight devices have been invented such as these disclosed in American patents U.S. Pat. Nos. 4,976, 923, 5,429,804 and 6,726,879. Test strips are fixed on covers of assay devices mentioned above and soaked into samples when the container is turned or tilted. An American patent published on Feb. 6, 2003, US2003/0027359A1 discloses a urine test cup. A column piston with a push rod is needed to make liquid samples flow out of the cup chamber and moisten the test element after the cover of the urine test cup closes the opening thereof. A Chinese patent application 200510113977.5 discloses a urine test cup which leads liquid sample to flowing from a collecting chamber to an assay chamber after the cover of the urine test cup closes the opening thereof. Another Chinese patent application 200480033286.8 also discloses a urine test cup which starts the test after the cover of the urine test cup closes the opening thereof. All said conventional devices have to be handled by those skilled in the art.

Recently, such assay devices are used more and more widely by common family or nonprofessional institutes. The test results have to be assessed by nonprofessionals, so a simpler operation procedure needs to be designed for these devices with accurate test results.

As a result, an assay device simple to operate with accurate test result is needed in the market. This invention provides an assay device meeting such needs.

SUMMARY OF THE INVENTION

This invention provides an assay device which is simple to operate and has an indication function. In particular, the device comprises a collecting chamber with an opening, test elements and an indication structure. The device indicates the operator through sound, in particular, by the vibration generated when the indication structure moves back to the original position after deformation. Preferably the vibration of indication structure attenuates naturally, not encountering any block or obstacle; therefore the sound generated by vibration is loud and lasting. In an optimized example, the indication structure will not contact any object or part.

In some embodiments, the indication structure at least comprises two elements which deform each other by pressing and then suddenly detach from each other, creating the sound through vibration when the elements move back to original state, i.e. the state before deformation. Preferably the two elements neither contact each other, nor other objects or parts while vibrating.

In some more detailed embodiments, the assay device comprises the cover body for closing the collecting chamber, the two elements of the indication structure which are arranged on the collecting chamber and the cover body respectively. The elements vibrate to create sound when the cover body seals the collecting chamber, i.e. the cover body reaches the special position of the collecting chamber. In some more specific embodiments, when the cover body is getting into the collecting chamber, two elements which are separated from each other previously begin to contact and deform each other gradually; the two elements suddenly detach from each other as the pressure disappears, and would recover the previous state before deformation, i.e. original position, creating sound by vibration. When the cover body closes and gradually seals the collecting chamber, the collecting chamber element and the cover body element which are previously not in contact now press each other. The pressed elements would deform, deviating from original position; when the cover body reaches a certain position, the two elements suddenly detach from each other. As the pressure generated by press disappears, the elements would move back to their position or state before deformation by vibrating, thereby create the indication sound. The sound indicates the cover body reaches the special position of the collecting chamber and seals the collecting chamber to prevent liquid sample from leaking.

In some preferred embodiments, a gap is designed just behind the cover body element to ensure longer vibration which creates louder and clearer sound. Preferably, the size of gap is larger than the amplitude of vibration of the collecting chamber element when the moves back to the original position after the cover body seals the collecting chamber. After the press between the cover body element and the collecting chamber element disappears, the collecting chamber element just falls into the gap. Thus the element vibration attenuates slowly in the gap while its amplitude or frequency not affected by any obstructor, which leads to louder and more lasting sound.

On the other hand, the cover body element can partially deviate from the cover body for the gap behind or near the cover body element. Therefore the vibration amplitude becomes larger to create louder sound after the force on the cover body element disappears, which may be resulted from the resonance of the collecting chamber element and the cover body element. Therefore, the gap behind the cover body element can substantially enhance the indication function of the present invention.

In some embodiments, the elements arranged respectively on the collecting chamber and/or the cover body can be of resilient elements, i.e. one resilient element or two resilient elements. The collecting chamber element and/or the cover body element deform each other when the cover body is closing the collecting chamber, and vibrates to create sound when the elements moves back to their original positions.

The "resilient element" said in this invention is a relative concept, which is opposite to "non-resilient element". In general, the modulus of resilience of resilient elements is less than that of non-resilient elements. For instance, the resilient element is made of plastic and the non-resilient element is made of metal such as iron, steel or lead. When force is applied between the plastic element and non-resilient element, the modulus of resilience of the resilient element is less than that of the non-resilient element, which means the resilient element is easier to deform than the non-resilient element when the force is applied to both. When the force applied suddenly disappears, the resilient element trends to recover, thereby creating sound by knocking or vibrating. It is common that the force applied to the resilient element is smaller than the limit of resilience thereof, so the resilient element can recover by itself after the external force removed. Both selectable resilient element and non-resilient element are made of plastic.

The resilience of the collecting chamber element and/or the cover body element can be the same or different. In a detailed embodiment, the resilience of the collecting chamber element is larger than that of the cover body element. In this case, the sound is mainly generated by vibration of the collecting chamber element. While in another embodiment, the resilience of the cover body element is larger than that of the collecting chamber element. At this time, the sound is mainly generated by vibration of the cover body element.

In a preferred embodiment, the cover body element is arranged on the external surface, which comprises a gradually rising slope. When moving from down to up, the collecting chamber element bends or distorts in the direction far away from the cover body surface, and at the same time, the cover body element bends or distorts towards the inner side of cover body. The collecting chamber element, however, can be arranged either on the internal surface or external surface thereof.

In a preferred embodiment, a square gap is designed behind the slope element on the cover body to ensure generation of enough loud sound. Less contact area between the cover body and the slope element thereon increases the possibility of deformation of the slope element and the aptitude of the element, thereby creating louder sound.

The cover body can close the collecting chamber opening by rotation. In an embodiment, the collecting chamber relative to the cover body rotates anticlockwise, and the cover body relative to the collecting chamber rotates clockwise. Preferably, the collecting chamber element relative to the cover body cannot further rotate clockwise when the collecting chamber element crosses the cover body element; or the collecting chamber element relative to the cover body can rotate clockwise, when the collecting chamber element crosses the cover body element In a specific embodiment, the way the cover body closes the collecting chamber opening is rotation. The opening comprises the internal thread matched with the cover body and the cover body comprises the external thread matched with the opening. The cover body element is arranged on the external surface of the external thread end; while the collecting chamber element is arranged the internal side thereof.

In another specific embodiment, the cover body also closes the collecting chamber opening by rotation. The external surface of the opening comprises the thread matched with the cover body and the cover body comprises the internal thread matched with the opening. In such case, the cover body element is arranged on the outside thereof; while the collecting chamber element is arranged at the thread end of the opening thereof.

In some preferred embodiments, when the cover body reach a special position, the indication structure starts to calculate the time needed to read the test result of the sample on the test element; in some other preferred embodiments, when the cover body reaches a special position, the indication structure indicates that the cover body has sealed the collecting chamber opening.

For some devices, the liquid sample in collecting chamber contacts the test element once the cover closes the collecting chamber opening. In use of conventional urine test cups, the start time needs to be recorded to read the test result of sample on test element in assay area after certain time. No uniform standard specifies when operators begin to record the time. Therefore, the operators may obtain different test results with the same device. The assay device of this invention has the advantage that the indication structure creates sound to inform the operator of starting to record the time needed to read the test result of the sample on the test element when the cover body reaches the special position of the collecting chamber.

It is sure that the device of this invention can indicate if the cover body seals the collecting chamber opening. Different operators, especially non-professionals may cause different tightness between the cover and the cup which leads to the cup opening incompletely sealed with the cover, even the liquid sample probably leaking from the cup for some devices. In this invention, the indication structure indicates the cover seals the collecting chamber opening when the cover reaches the special position of the collecting chamber (it is believed that the cover body at the position can completely seal the collecting body opening). At this time, the operators don't need to continue closing the collecting chamber. Thus, operators don't need to worry the leakage problem or damage to the cup and the cover resulted from excessive closure because all device openings can be completely sealed.

In addition, the assay device also can indicate the following, for example if enough liquid is collected, or if the sample contacts the test element, or if the next procedure begins and so on.

The collecting chamber and the cover can be made of plastic such as ABS or PP. The elements arranged respectively thereon can be made of the same material as the collecting chamber and the cover. In a detailed embodiment, the cover body and the element thereon are made of acrylonitrile-butadiene-styrene copolymer; and the collecting chamber and the element thereon is made of polypropylene.

For conventional similar assay devices, at present, the collecting chamber opening is combined with the assay chamber opening if the cover body is designed to close the connected opening, which means the collecting chamber opening is as high as the assay chamber opening at the collection point. So both the collecting chamber opening and the assay chamber opening are closed by the cover body at the collection point. However, the opening of assay chamber is often sealed with a film or foil materials, which may damage the connected opening. Moreover, the opening at connection point is a little higher than the collecting chamber opening after the assay chamber opening is sealed with the film. Thus the collecting chamber is not completely sealed by the cover body at the risk of leakage. In a optimized embodiment, the collecting chamber opening is separated from the assay chamber opening at the connection point. Preferably, the assay chamber opening is a little higher than the collecting chamber opening. In another preferred embodiment, the edge of collecting chamber opening of the split-type device is a little wider than that of the combined-type device, but not less than that of the cover body closing the collecting chamber.

On the other hand, this invention also provides a method for testing an analyte in samples, including an assay device which comprises a collecting chamber with an opening, a test element and an indication structure. The indication structure deforms and then creates sound by vibration when it moves back to its original position. In a preferred embodiment, the indication structure does not contact any subjects or parts.

In another specific embodiment, the indication structure comprises two elements which contact and deform each other, and then detach from each other. The detached elements vibrate to generate the indication sound when the elements trend to move back to their original position. In a preferred embodiment, the two elements do not contact any subjects or parts while vibrating after detaching from each other.

In a specific embodiment, the device further comprises the cover body closing the collecting chamber; the two elements of the indication structure are arranged on the collecting chamber and cover body respectively. In a preferred embodiment, the device also comprises a gap just behind the cover body element.

In another embodiment, the cover body element is arranged on external surface thereof, comprising a gradually rising slope. When moving from down to up, the collecting chamber element bends or distorts in the direction far away from the cover body surface, and/or the cover body element bends or distorts towards the inner side of cover body; and then the collecting chamber element moves from the top of the cover body slope element into the gap behind the slope.

In a specific embodiment, operators can record the time needed to read the test result of sample on the test element when he/she hears the sound the indication structure creates.

Benefits

The device and the method of this invention make operation procedures simpler, which is appropriate for non-professionals and provides more accurate test results.

BRIEF DESCRIPTION OF THE DRAWINGS

FIG. 6-FIG. 8 are working projection views of the indication structure of an embodiment in this invention; wherein

DESCRIPTIONS OF MARKS

Assay device 400; collecting chamber 100; the collecting chamber opening (opening) 102; edge of the collecting chamber opening 1022; edge of the collecting chamber opening and the assay chamber at connecting point 1021; side wall of collecting chamber 105; shared side wall of the collecting chamber and the assay chamber 1051; inside wall of the collecting chamber 101; bottom of the collecting chamber 106; indication structure element on the collecting chamber 103; side wall of the collecting chamber element 1031, 1033, 1034; bottom of the collecting chamber element 1032; closing thread of the collecting chamber 104; assay chamber 200; assay chamber opening 201; sealing surface of the assay chamber opening 203; edge of the assay chamber opening 202; edge of the connected opening of the assay chamber and the collecting chamber 2021; cover body 300; cover edge 301; cover body thread 304; indication structure element of the cover body 302; cover body gap 303; side of cover body gap 305, 306 (3023); slope of the cover body element 3021; sides 3022, 3023 (306);

Description of the Preferred Embodiment

Structures or technical terms the utility model relates to are further described as follows Sample The assay device of this invention can test any form of samples, including body fluid (e.g. urine, other body fluid and clinic samples). Liquid samples can be collected from solid or semi-solid samples including feces, biological tissues and food samples. These solid or semi-solid samples can be transferred into liquid samples by any method. For example, solid samples are mixed, broken, dipped soft, incubated, dissolved or decomposed by enzymolysis (e.g. water, phosphate buffer or other buffer). "Biological samples" include samples from animals, plants and foods as well as urine, saliva, blood, blood components, cerebrospinal fluid (CSF), vaginal swab, semen, feces, sweat, secretion, tissue, organ, tumor, culture of tissue and organ, cell culture and medium thereof (human or animals). Food samples cover samples from any plant, plant tissue, plant cell culture and medium thereof. "Environment samples" refer to samples from natural environment (e.g. lake water or other water body sample, sewage sample, soil sample, underground water sample, ocean water sample and waste water sample). Sewage and relevant waste can also be incorporated into the environment sample.

Analyte

The assay device of this invention can be used for analyzing any analyte. The device of this invention can be used for stable determination of the following examples including (but not limited to them): human chorionic gonadotropin (hCG), luteinizing hormone (LH), follicle-stimulating hormone (FSH), hepatitis C virus (HCV), hepatitis B virus (HBV), hepatitis B surface antigen (HBsAg), human immunodeficiency virus (HIV) and any abused drug. The analyte can be detected in any liquid or liquefied samples, e.g. urine, saliva, blood, plasma or serum. Other analytes include creatinine, bilirubin, nitrite, protein (non-specificity), blood, leukocyte, blood glucose, heavy metal, toxin and bacteria (e.g. protein and sugar of some specific bacteria such as *escherichia coli* 0157:H7, *staphylococcus aureus, salmonella, clostridium perfringens, campylobacter, L. monocytogenes, vibrio parahaemolyticus* or *bacillus cereus*). Any other analyte appropriate for side stream experiment can be assayed by this device. The analyte can also be contagious material or substances that indicate the infective stage. Analytes can also be drug (drug of abuse), hormone, protein, DNA, RNA, nucleic acid molecule and pathogen. Drug of abuse (DOA) refers to use of drug for non-medical purposes (often for nerve paralysis). Abuse of these drugs can lead to physical and mental damage, drug dependence, drug addiction and/or death. These drugs include cocaine, amphetamine (e.g. black beauties, white amphetamine tablet, dextroamphetamine, dextroamphetamine tablet and Beans), methamphetamine (crank, meth, crystal and speed), barbiturate (Valium®, Roche Pharmaceuticals, Nutley and New Jersey), sedatives (sleep auxiliary drug), lysergide (LSD), inhibitors (downers, goofballs, barbs, blue devils, yellow jackets and methaqualone), tricyclic antidepressants (TCA, i.e. imipramine, elavil and doxepin); phencyclidine (PCP), tetrahydrocannabinol (THC, pot, dope, hash, weed and so on) and opiate preparations (morphine, opium, codeine, heroin and hydrocodone). The test strip can also be used for detection of drug that is applied to medical use but is easy to overdose, such as tricyclic antidepressants (imipramine or the similar) and acetaminophen.

Test Element

Test element can be test strip flowing widthwise to detection of a plurality of analytes. It is sure that other appropriate test elements can be also used in this invention.

Various test elements can be combined for this invention. One form of test elements is test strip. Various forms of test strips can be used for analyzing analytes in samples (e.g. drug or metabolites reflecting physical conditions), such as immunoassay or chemical analysis. The test strips can be in the form of non-competitive or competitive analysis pattern, comprising absorbent material of a sample feeding area, a reagent area and a test area. The samples are added into the sample feeding area and flow to the reagent area by a capillary tube. The sample will combine with the reagent if the analyte exist in the sample, and then flow to the test area. For other reagents, the molecules of specifically binding analyte may be fixed in the test area. These reagents can react with the analytes in the samples (if present) and bind the analytes in the test area, or the analyte binds one of reagents in the reagent area, which indicates the marker for indicating signals is present in the reagent area or the separated marking area.

In the typical noncompetitive analysis pattern, signals are produced if the analyte is present in the sample, and vise versa. In the competitive analysis pattern, signals are produced if the analyte is not present in the sample, and vise versa.

The test element is of test strip that can be made of absorbent or nonabsorbent materials. The test strip can be composed of a plurality of materials for transferring liquid samples, wherein one of material of test strip can cover another material, such as filter paper covering nitrocellulose film. An area of the test strip can be made of one or a plurality of materials, while the other area can be made of different one or a plurality of materials. The test strip can be adhered to certain support or hard surface to improve the strip holding strength.

The analyte is detected through the signal generating system. If one or a plurality of enzymes that have specific reaction with the analyte is applied with the above method that the specific binding material is fixed on the test strip, one or a plurality of combined materials of the signal generating system is fixed on the analyte test area of test strip. The signal generating material can be arranged on the sample feeding area, the reagent area, the test area or the whole test strip, and can also be added to one or a plurality of materials of the test strip. The solution containing the marker is added into the test strip surface, or one or a plurality of materials of the test strip are immersed into the solution containing the marker. And then the test strip added with the solution containing the marker is dried.

The areas of the test strip can be arranged by the following sequence: the sample feeding area, the reagent area, the test area, the control area, the adulterant testing area and the liquid sample absorbing area. The control area is arranged behind the test area. All areas can be on the test strip made of the same material, and also be on the strip made of different materials. All areas can directly contact liquid samples, or the end of each area overlaps the front of the next area in the liquid sample flowing direction. The test strip can be made of good absorbent material such as filter paper, glass fiber or nitrocellulose film and so on. The test strip can be also in other forms.

Assay

Assay means to test or detect if one substance or material is present, but not limited to this, e.g. chemicals, organic compounds, inorganic compounds, metabolites, drugs or drug metabolites, the organic tissue or organic tissue metabolites, nucleic acids, proteins or polymers. In addition, assay can also determine the quantity of substance or material. Furthermore, assay also includes immune detection, chemical detection, and enzyme assay and so on.

Assay Device

In a specific example, the assay device 400 comprises a collecting chamber 100 for collecting and storing liquid samples. The collecting chamber 100 consists of the side wall 105, the bottom 106, and an opening 102 for importing liquid sample. 'One' mentioned in the specifications, abstract and claims of this invention shall be understood as at least one, or one in quantity, but not understood as 'unique' or 'only one'. For example, the assay device comprises an indication structure, but the assay device comprises 2 or more indication structures are also obviously incorporated into the claims of this invention, and shall not be excluded. The assay device can further comprise an assay chamber 200 that has a test element. The liquid sample can flow freely or under control in the collecting chamber, and contact the test element in the assay chamber; the chemical reagent on the test element can detect if an analyte is present in liquid sample or determine the quantity of the analyte. The assay device 400 can further comprise the cover body 300 that is used for closing the collecting chamber opening 102. In a detailed embodiment, the assay device comprises an indication structure which can indicate whether the cover body 300 reaches a specific position, and more specifically indicate whether the cover body closes the collecting chamber 100 at a special position. The cover body 300 closes the collecting chamber 100 by a plurality of ways such as thread. For example, the collecting chamber opening 102 comprises the external thread and the cover body comprises the internal thread matched with the external thread; when the cover body closes the collecting chamber, the opening is sealed by counter rotating. In addition, the cover body can be inserted into the opening to seal the collecting chamber opening 102 in the form of piston. Or the cover body can close the collecting chamber by fastener. A sealing ring can be arrange on the cover body or at the connecting position of cover body edge and collecting chamber edge so that the cover body can effectively seal the collecting body opening. In a detailed embodiment, the sealing ring is 0 ring.

The indication structure can also be applied to other assay devices, particularly devices containing the cover body which is used for sealing the collecting chamber opening; such similar devices have been specifically described in some disclosed American patents as U.S. Pat. Nos. 7,270,959, 7,300,633, 7,560,272, 7,438,852, 4,976,923, 5,429,804 and 6,726,879. The indication structure disclosed in this invention can be applied to an embodiment of all devices disclosed in the above patents as an example of this invention.

Indication Structure

In a specific embodiment, the indication structure can be arranged on the assay device 400 to create indication sound. The sound can be "pop", "bang", "boom", "ding-ding", "crackle" or any other proper sound.

In some other embodiments, the cover body seals the collecting chamber opening by counter rotation of the cover body and the collecting chamber. One part of the indication structure is arranged on the cover body 300, and the other part of the indication structure is arranged on the collecting chamber wall 100. When the cover body rotates to close the collecting body opening, the part of the indication structure on the cover body and the part of the indication structure on the collecting chamber deform each other by interaction. After the force disappears, the deformed parts would like to move back to the original position so as to create sound by vibration.

In this invention, the cover body element 302 and the collecting chamber element 103 can have resilience: both can have resilience or one of the two has resilience. In an embodiment, the resilience of the cover body element 302 is better than that of the collecting chamber element 103 (or the cover body element has resilience, but the collecting chamber element does not have resilience), the deformation of the cover body element is larger than that of the collecting chamber element at this time (or collecting chamber element doesn't deform), thereby the cover body element creating louder sound than the collecting chamber element. In such case, a square gap is arranged on the cover body element so that the element detaches from the cover body as far as possible to ensure the indication effect, i.e. larger deformation of the cover body element 302, and louder sound by vibration. In another embodiment, the resilience of the collecting chamber element 103 is better than that of the cover body element 302 (or the collecting chamber element has resilience, but the cover body element does not have resilience), the deformation of the collecting chamber element is larger than that of the cover body element at this time (or the cover body element does not deform), so the sound is mainly created by vibration of the collecting chamber element 103.

In this invention, the cover body element and the collecting chamber element can be made of a plurality of materials, often plastic, PVC, PP, ABS and so on. The material of the cover body element can be the same as or different from the material of the cover body. The same material is recommended considering the cost. In the same way, the material of the collecting chamber element can be the same as or different from the material of the collecting chamber. The preferred is the same material. The indication structure element and the assay device element can be separately manufactured, and then fixed on the internal surface of the collecting chamber and the external surface of the cover body thread by adhesive bonding. Preferably, the collecting chamber and cover body can be one-time injected with different materials, such as the cover body is made of Acrylonitrile-Butadiene-Styrene (ABS) and the collecting chamber is cast with polypropylene (PP).

Description of the Preferred Embodiment

An embodiment of this invention is specifically described in structure and use method thereof.

Figure 1:
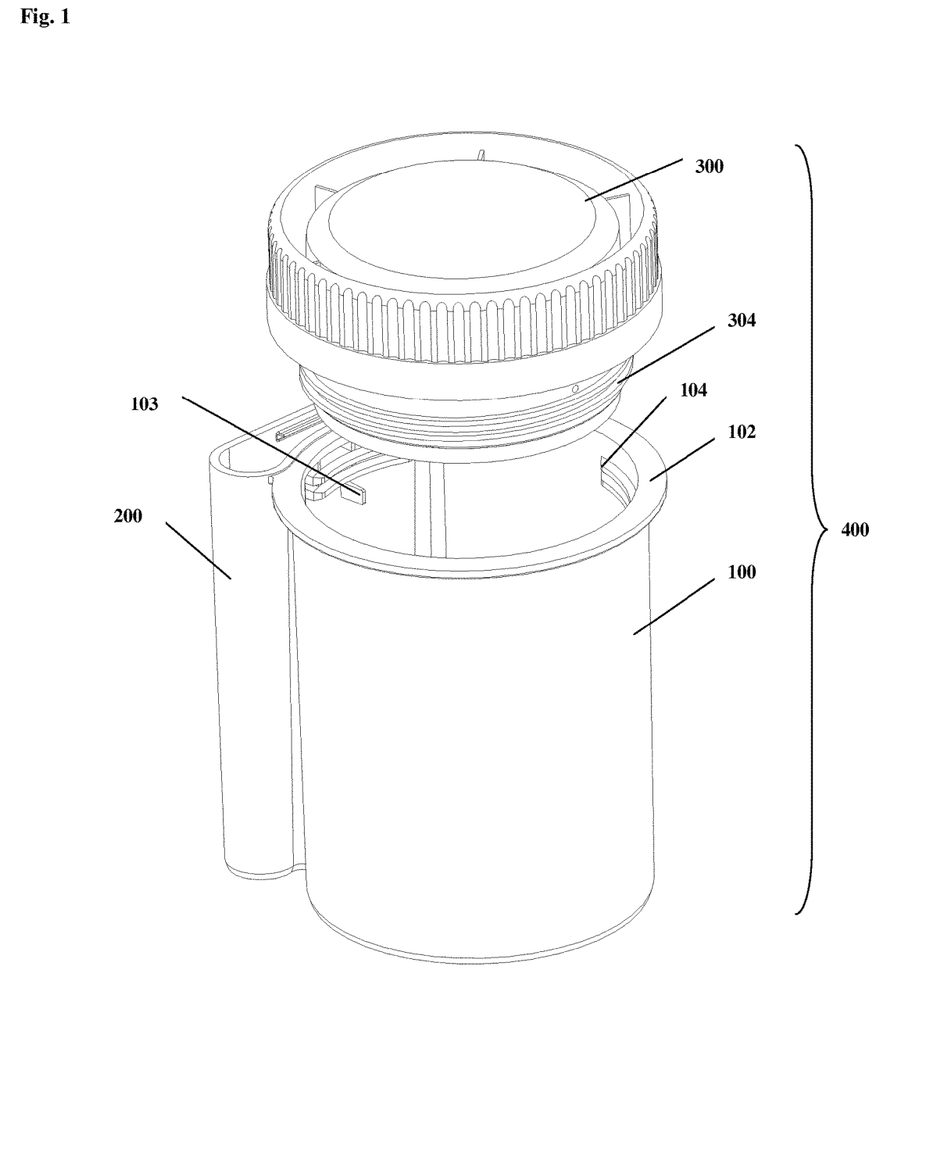
FIG. 1 is a schematic view of an embodiment of the assay device in this invention.
Figure 2:
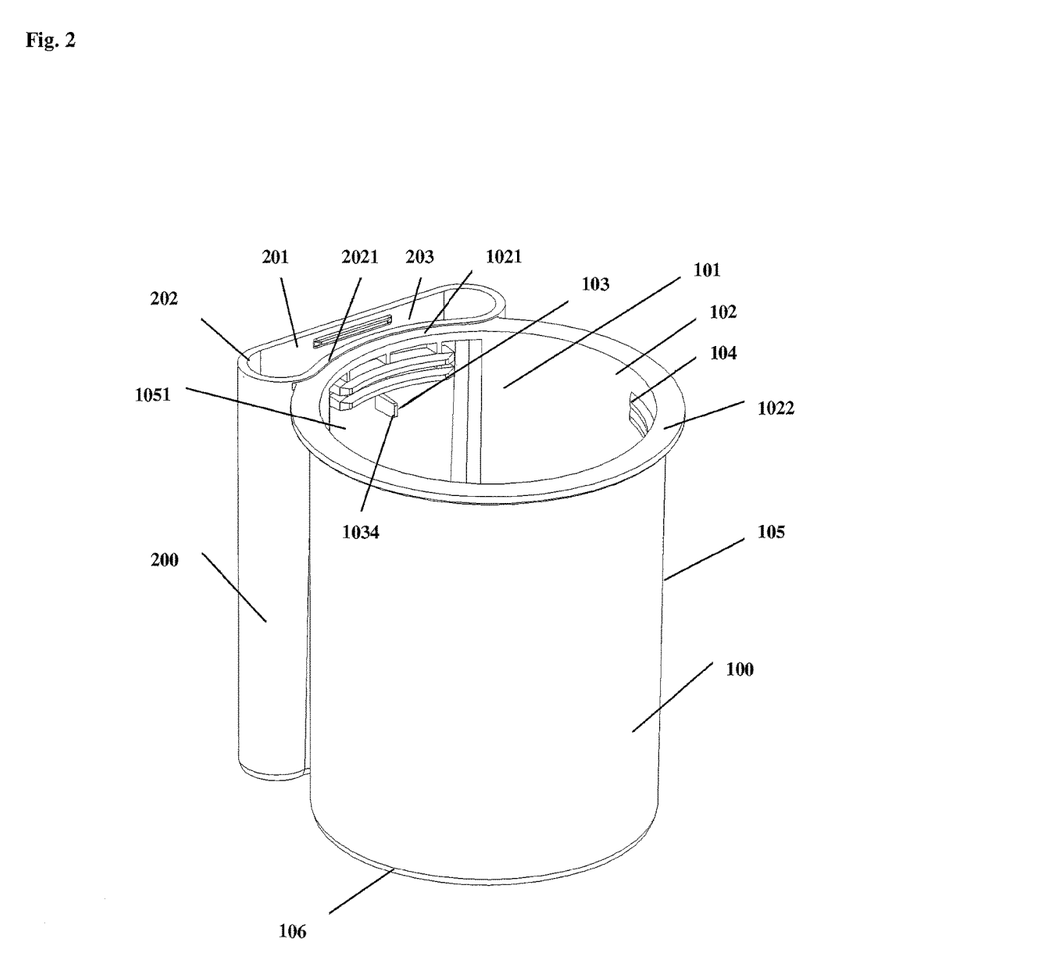
FIG. 2 is a schematic view of the collecting chamber of an embodiment in this invention, wherein the indication structure is arranged on the inside wall of the collecting chamber.
Figure 3:
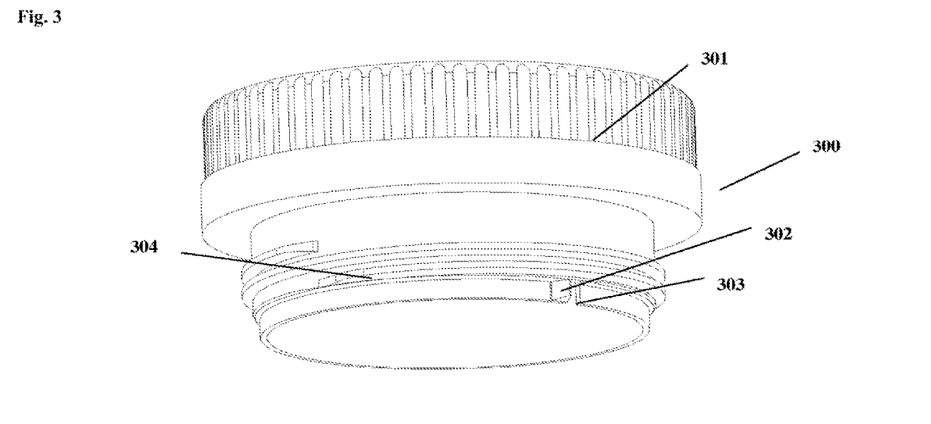
FIG. 3 is a schematic view of the cover body of an embodiment in this invention, wherein the indication structure element is arranged on the external surface of the cover body thread.

As shown in FIG. 1, the assay device 400 comprises a collecting chamber 100, an assay chamber 200 and a cover body 300, wherein the assay chamber and the collecting chamber can be connected by a plurality of ways such as direct communication and indirection communication (e.g. communication by pipe). The assay chamber and the collecting chamber can be separated or combined together. In this embodiment, the assay chamber 200 and the collecting chamber 100 is combined to share the same wall 1051. As shown in FIG. 2, the collecting chamber 100 comprises the chamber bottom 106 and side wall 105 and further comprises the opening edge 1022 connected with the side wall 105. The collecting chamber 100 can contain liquid samples. The collecting chamber 100 further comprises the chamber opening 102, through which the liquid sample can enter into the collecting chamber 100. The inside wall of the collecting chamber 101 is arranged with the internal thread 104 and the collecting chamber element 103 (part of the indication device). The assay chamber 200 also consists of the bottom, the side wall and the chamber opening 201. The assay chamber 200 and the collecting chamber 100 share a part of side wall 1051, and the assay chamber opening 201 has the opening edge connected with the side wall, as shown in FIG. 2, wherein the assay chamber opening is sealed. In a detailed example, an aluminum foil can be welded on the opening edge of the assay chamber 202 to seal the assay chamber 200 and form an opening sealed surface 203. In FIG. 3, the cover body 300 comprises the cover edge 301 and the external thread 304. The external thread of the cover body 304 comprises an indication structure element 302 and a gap 303 which is closely adjacent to the element 302. The gap 303 can be also a part of the indication structure.

Figure 4:
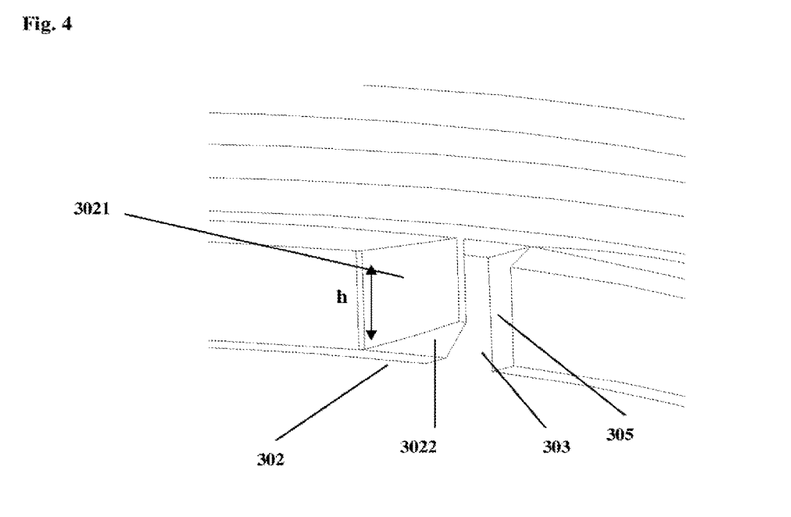
FIG. 4 is an enlarged view of the cover body indication element of the assay device of an embodiment in this invention.
Figure 5:
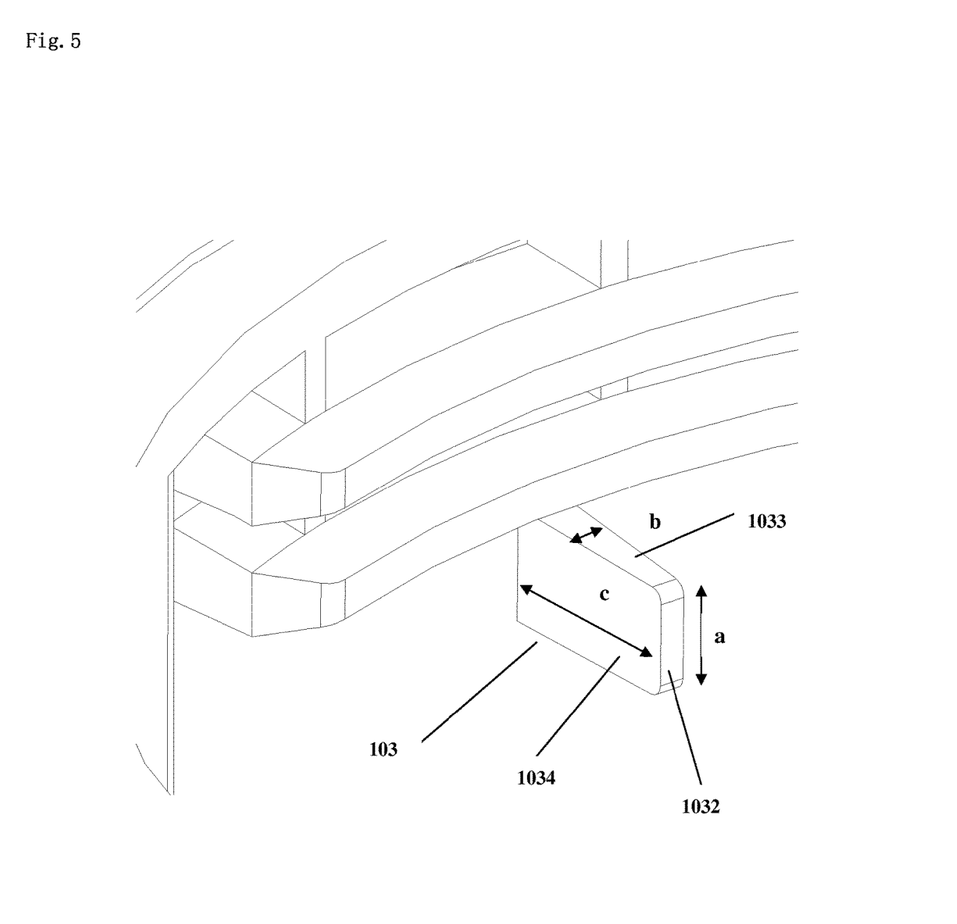
FIG. 5 is an enlarged view of the collecting chamber indication element of the assay device of an embodiment in this invention.

The indication structure comprises the collecting chamber element 103 and the cover body element 302, and can comprise the gap 303 closely adjacent to the cover body element 302. The collecting chamber element 103 can be of a square column projection as shown in FIG. 1, FIG. 2, FIG. 5, and from FIG. 9 to FIG. 14. The square column element 103 comprises the side wall, 1031, 1033, 1034 and the bottom 1032. As shown in FIG. 5, the height (c) from the square column 103 to the inside wall of the collecting chamber 101 shall not be higher than the projection height of the internal thread 104 of the collecting chamber. In a detailed embodiment, the height (c) of the element 103 is a little lower or equal to the projection height of the internal thread 104. The length (a) of the square column element 103 is not longer than the distance from the collecting chamber bottom 106 to the internal thread 104; the length is can range from 2 mm to 10 mm to ensure the created sound loud and clear; preferably, the length (a) is 4 mm, the same as the width of the cover body thread bottom 304. The thickness of the square column element 103 (width b) can range from 0.5 mm to 3 mm. In a specific embodiment, the width is 1 mm. In a preferred embodiment, the width (b) of the square column 103 can be increasingly reduced from the bottom (connected to the collecting chamber) to the end, for example, as shown in FIG. 5, the bottom is 2 mm wide and the end is reduced to 1 mm wide. As shown in FIG. 4, the cover body element 302 can be arranged at the end of the cover body thread 304, an inclined projection, comprising a slope 3021 and a side 3022. The width (h) of the slope element 3021 can be less than or equal to the width of the cover body thread bottom 304. The top of the slop 3021 shall not be over the projection height of the thread 304. Under the circumstances, the steeper slope can create better sound to ensure the indication sound effect. The indication structure can comprise the gap 303 arranged on the cover body which is closely adjacent to the cover body element 302. Therefore, one side of the gap 306 is the side 3023 of the cover body element 302, and the other side of the gap is marked 305. The gap 303 can ensure the collecting chamber element 103 is not limited at vibration in the amplitude and frequency to guarantee the time and strength of sound. So people can hear enough loud and clear sound to improve the indication sound effect of the indication structure. Preferably, the gap is wider than the vibration amplitude of the collecting chamber element 103 (i.e. the distance from the side 306 to the other side 305) to leave enough space for the element 103 vibrating to ensure the sound effect.

Figure 6:
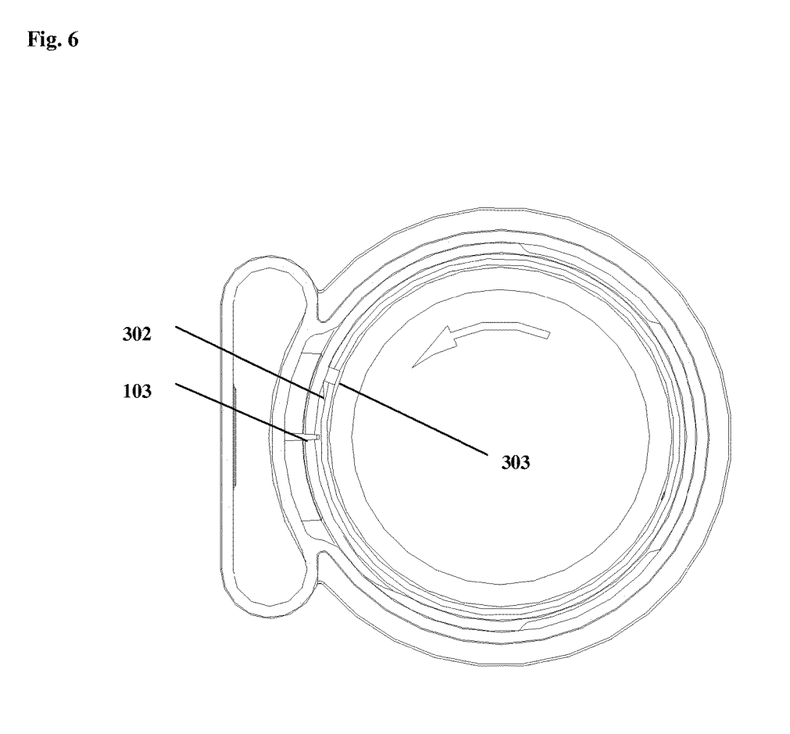
FIG. 6 shows the state that the two elements do not contact each other.
Figure 7:
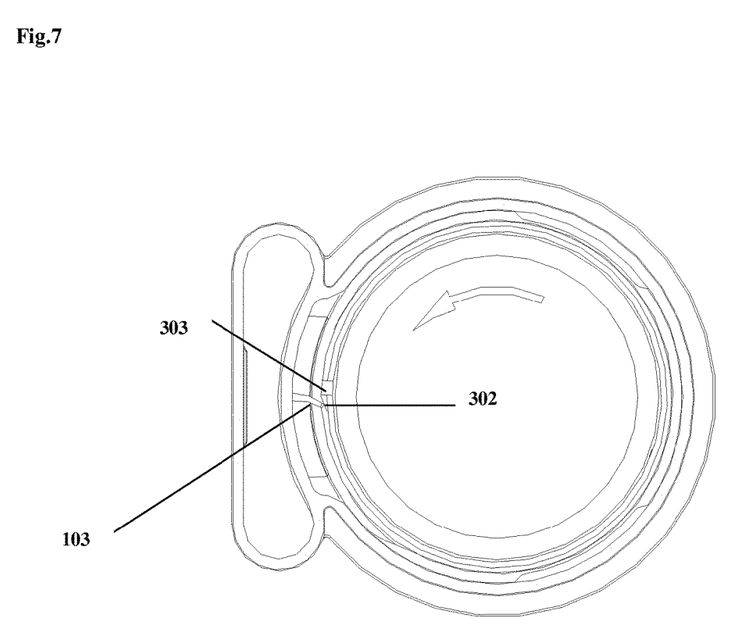
FIG. 7 shows the moment that the two elements are contacting each other.
Figure 8:
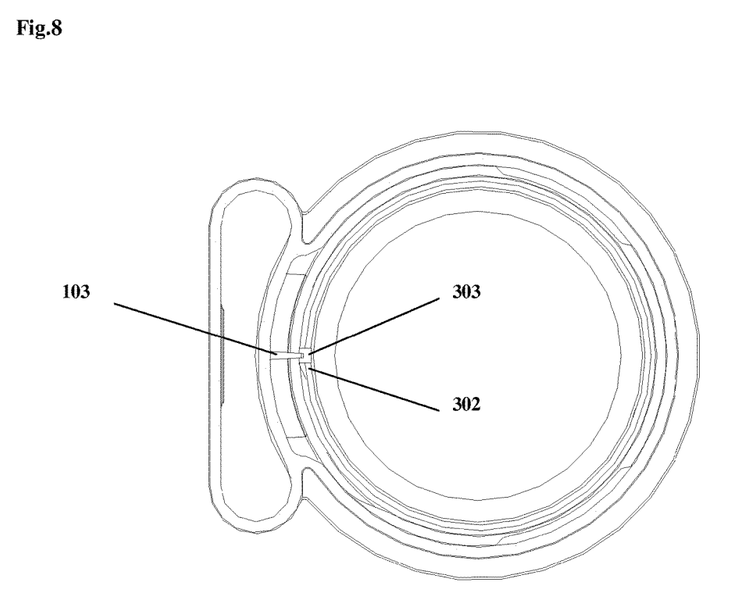
FIG. 8 shows the state the two elements detach from each other after contacting.

When the collecting chamber 100 contacts the cover body 300, the indication structure starts to work. When the cover body 300 closes the opening 102 of the collecting chamber 100, the end element 302 of the cover body thread 304 start to contact the end element 103 of the internal thread 104 on the collecting chamber as the cover body thread 304 gradually matches the internal thread 104 on the collecting chamber, shown as FIG. 6, FIG. 7 and FIG. 8. The collecting chamber element 103 and the cover body element 302 do not contact each other at first (FIG. 6), then contact and deform each other (FIG. 7), and detach from each other when the pressure is removed. The collecting chamber element 103 enters into the gap 303 of the cover body element 302 (FIG. 8). After the pressure disappears, the collecting chamber element 103 and/or the cover body element 302 previously deformed have to recover, so the collecting chamber element 103 and/or the cover body element 302 vibrate to move back to the original position. The sound is created during vibration for indication.

Figure 9:
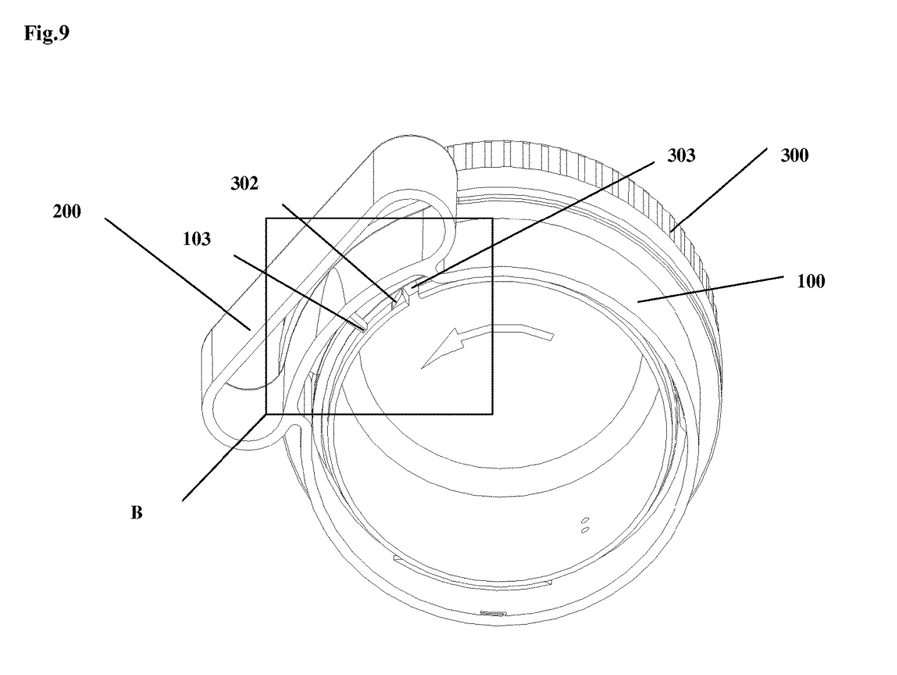
FIG. 9 is a sectional view of the indication structure elements that do not contact each other of an embodiment in this invention.
Figure 10:
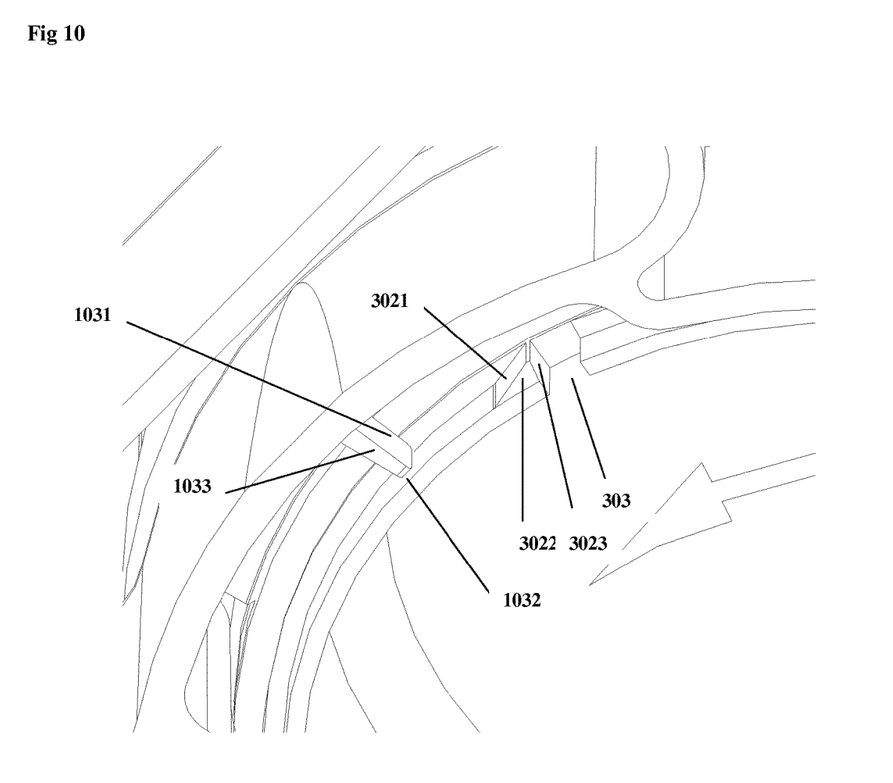
FIG. 10 is a partial enlarged view of B part of the indication structure in FIG. 9.
Figure 11:
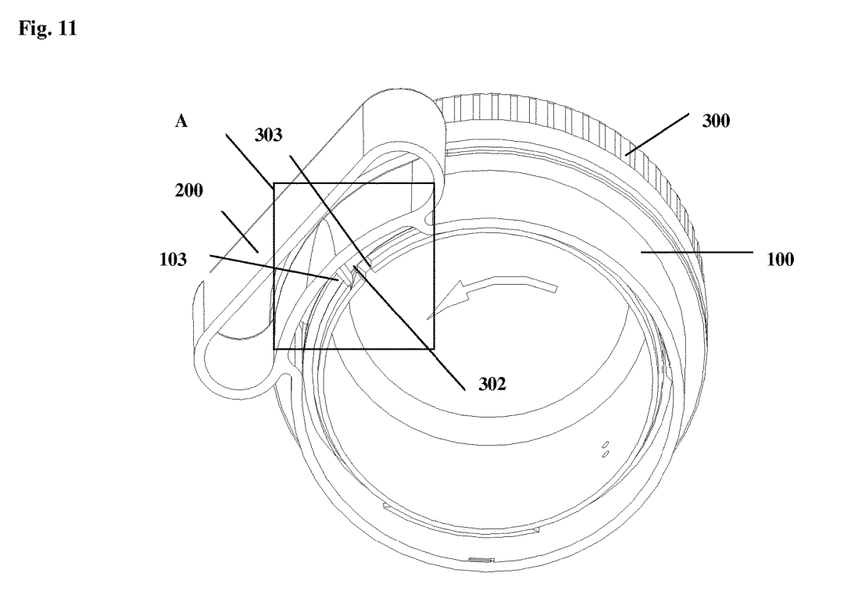
FIG. 11 is a sectional view of the indication structure elements that contact each other of an embodiment in this invention.
Figure 12:
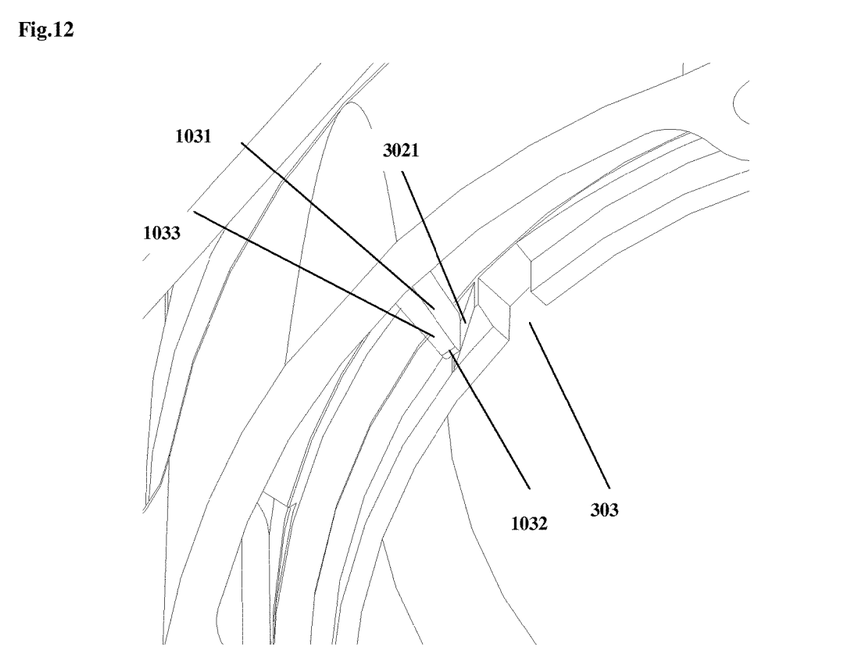
FIG. 12 is a partial enlarged view of A part of the indication structure in FIG. 11.
Figure 13:
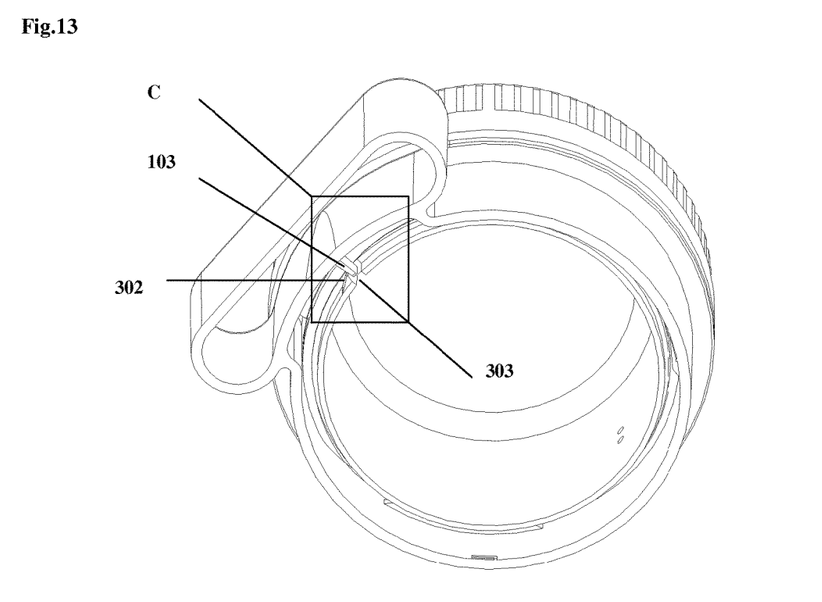
FIG. 13 is a sectional view of the indication structure elements that detach from each other of an embodiment in this invention.
Figure 14:
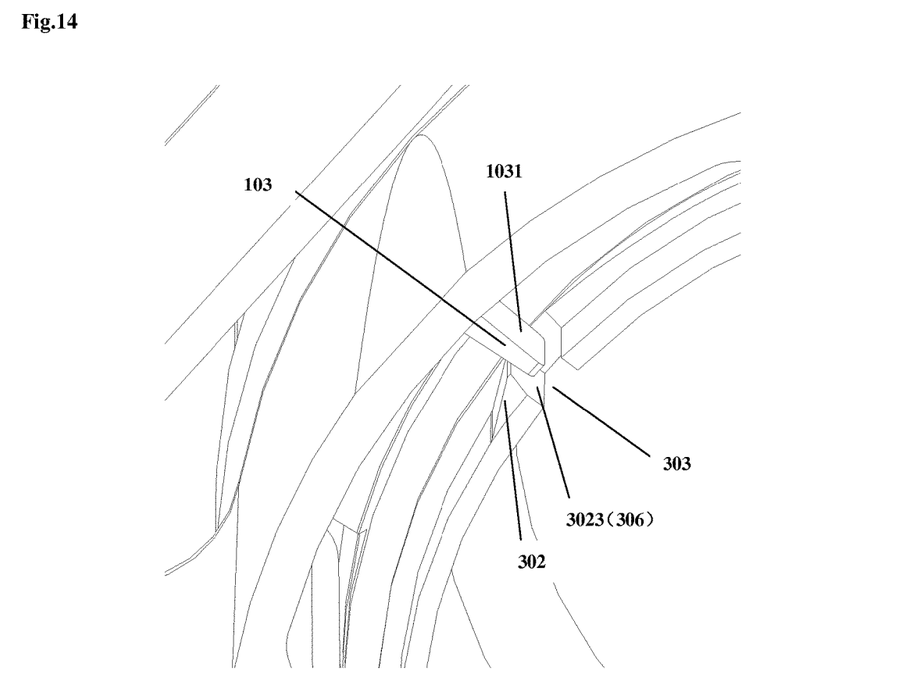
FIG. 14 is a partial enlarged detail of C part of the indication structure in FIG. 13.

FIG. 9-FIG. 14 shows the working status of the indication structure elements as the indication structure works. When the cover body 300 closes the collecting chamber opening 102, the start point of the cover body thread 304 begins to contact the start point of the internal thread 104 of the collecting chamber. When the cover body 300 is rotated, the two threads 104 and 304 gradually match each other. FIG. 9 and FIG. 10 (the amplified view of the indication structure) show the cover body element 302 and the collecting chamber element 103 are on the verge of contact when the cover body 300 and the collecting chamber 100 reach a specific position. When the cover body 300 is further rotated, the bottom 1032 on the collecting chamber element 103 starts to contact the slope 3021 of the cover body element 302 and slides on the slope 3021, as shown in FIG. 11 and FIG. 12. The pressure between the two elements 103 and 302 gradually increases with the element 103 sliding on the slope 3021 to a higher position. The collecting chamber element 103 is pressed to deform far away from the slope 3021, and/or the cover body element 302 also deforms or distorts towards the inside of the cover body 300. At this time, as the collecting chamber element 103 distorts, the side 1031 of the collecting chamber element 103 starts to contact the slope 3021. As shown in FIG. 13 and FIG. 14, when the collecting chamber element 103 slides to the top of the slope 3021 of the cover body element (the vertical side 3023 (306) is behind the slope 3021), the collecting chamber element 103 suddenly moves from the top of the slope 3021 to the gap 303 of the cover body (losing the support of the slope 3021) if the collecting chamber element 103 continuously slides due to the rotation of the cover body 103. At this time, the pressure between the two elements 103 and 302 suddenly disappears, the collecting chamber element 103 and/or the cover body element 302 previously deformed have to move back to the original position after the pressure removed (the initial state of the elements), so the collecting chamber element 103 and/or the cover body element 302 vibrate and move back to the original position by vibration. The sound created by vibration informs the operator that the cover body 300 has rotated to the specific position and the cover body 300 has sealed the collecting chamber opening, which means further rotation is not needed. Or the sound optionally informs the operator that he/she can start to account the time needed to read the test result of the analyte on the test element. Or the sound can indicate that the operator can proceed with the next procedure. The moment the cover body 300 seals the collecting chamber opening 102, and the moment the time needed to read the test result is counted can be simultaneous and can be different. The indication that the cover body reaches the specific position for operators can represent a plurality of meanings, for example, the sound represents the beginning of the next procedure, the beginning of test, the finish of the test or other meanings. The product instructions can optionally describe the sound indication and guide operators how to understand the indication meaning.

The specific position can be pre-set. For example, when the cover body seals the collecting chamber by rotation, the specific position can be set at the fixed circles that the cover body relative to the collecting chamber opening rotates from the contact position (e.g. for 1-5 circles, the cover body has sealed the collecting chamber opening). Specifically, the cover body is arranged with the external thread and the collecting chamber opening is arranged with the internal thread. The external thread and the internal thread have a geared interface (contact position). When the cover body and the collecting chamber are rotated, the geared external thread and inner thread helps the cover body move from high position to low position. The cover body is often arranged with a resilient sealing ring. When the resilient sealing ring contacts the cup edge, another 0.1-1 circle of rotation makes the sealing ring closely contact the cup edge, which means complete sealing. The gear position and the indication position shall be set on the cover body, so the position of another indication element on the collecting chamber element can be easily set by the thread rings or the distance between threads. Therefore, after the cover body rotates several circles, the two elements contact and create the sound just before or after the sealing ring seals the opening, thereby indicating that the cover body has sealed the opening and no further rotation is needed. In addition to the method above, the positions can be set by other ways. In this invention, the specific position can present that the assay device starts the assay except the cover body sealing the collecting chamber. For example, the assay device starts assay when the cover body rotates to the specific position, and the indication structure create sound to indicate the assay beginning when the cover body rotates to the specific position.

In another optional embodiment, the collecting chamber element 103 moves on the slope of the cover body element 302, drops into the back of the slope 3021 or the gap 303, and creates the sound by vibration when the elements move back to the original position. The cover body 300 and the collecting chamber 100 cannot make relative motion, but fixed on a position under the lock state. In a detailed embodiment, the cover body 300 cannot reversely rotate to open the collecting chamber opening 102 after the cover body 300 seals the opening 102. A method of fixing the cover body 300 is that the element 302 stops the collecting chamber element 103 reversely rotating. For example, the cover body 300 rotates clockwise to seal the collecting chamber opening 102, and the collecting chamber element 103 drops into the gap behind the cover body element 302 when the indication structure creates sound. The vertical side 3023 of the cover body element 302 can stop the collecting chamber element 103 moving, so the collecting chamber element 103 cannot rotate clockwise relative to the cover body 300. Therefore, the cover body 300 and the collecting chamber 100 are in the lock state. In this invention, "lock" refers to that the cover body 300 and the collecting chamber 100 are fixed as a whole, so the cover body and the collecting chamber opening cannot relatively move, which includes further rotation of the cover body to seal the collecting chamber opening, and reverse rotation of the cover body to open the collecting chamber opening.

In another optional embodiment, the collecting chamber element 103 drops into the back of the slope 3021 or the gap 303 after moving on the slope of the cover body element 302, and creates the sound by vibration when the element would move back to the original position. The collecting chamber opening 102 can be opened by reverse rotation of cover body 300 and the collecting chamber 100. For instance, the sound 'pop' the operator hears indicates the cover body has sealed the collecting chamber opening and the rotation can be stopped when the cover body is rotated into the specific position. At this time, other operations of the assay device can be performed to test the analyte in the sample. Surely, when hearing the sound created by the indication structure, the operator can count the time needed to read the test result of the analyte in the sample, e.g. 2-5 min later to read the test result of the analyte on the test element. Visual examination can directly show the color change or the color shade to determine the presentation and quantity of the analyte; or the machine can directly read the test result and automatically output the result. If the test liquid is found positive with these operation procedures (after the test is finished), the sample needs to be sent to a professional assay institution for determination. The operator at the professional assay institution can reversely rotate the cover body to open the collecting chamber and get the sample for further test.

In the invention, the conventional integrated structure of the collecting chamber opening and the assay chamber opening is innovated into split parts to ensure the sealing of collecting chamber. As shown in FIG. 2, the collecting chamber opening 102 and opening edges 1022, 1021 is not the same high as the assay chamber opening 201 and the opening edges 202, 2021 at the connecting point of the collecting chamber 100 and the assay chamber 200. The assay chamber opening is 0.1-0.5 mm higher than the collecting chamber opening. In a preferred embodiment, the assay chamber opening is 0.3 mm higher than the collecting chamber opening. Thus, when the assay chamber is sealed, particularly with a film or foil, the opening edge of the collecting chamber connected with the assay chamber can be prevented from damage. At the same time, the edge width of the connected opening of the collecting chamber and the assay chamber should be changed. In conventional integrated assay devices, the edge width of the connected opening of the two chambers is often the same as the thickness of the assay chamber opening to facilitate sealing the assay chamber opening with film materials. In the innovated structure, the circumference of the assay chamber (202 and 2021) is evenly wide; while the opening edge 1021 of the collecting chamber is slightly narrower at the connection than the other part of the edge 1022, but not narrower than the opening edge of the cover body 300 matched with the collecting chamber opening. In a preferred embodiment, the 1.5 mm wide connected opening of the integrated structure is changed into 1.5 mm wide opening edge of the assay chamber (the opening edge of the assay chamber 2021) and 3 mm wide opening edge of the collecting chamber (the opening edge of the collecting chamber 1021) at connected opening.

The invention claimed is:

1. An assay device for testing an analyte in a sample, comprising:
    a collecting chamber with an opening for collecting the sample;
    a test element;
    a cover body closing the opening of the collecting chamber, the cover body having an external surface having an external spiral thread structure;
    a cover body element disposed on the external surface adjacent the external thread structure; and
    an indication structure operable to create sound through vibration, the indication structure having the cover body element disposed on the external surface adjacent the external thread structure and a collecting chamber element disposed on an inner surface of the collecting chamber, wherein the cover body element and the collecting body element engage and detach each other thereby generating a sound when the cover body is threaded onto the collecting chamber from a first position to a second position, and wherein a portion of the collecting body element freely vibrates within a gap disposed on the external surface of the cover body adjacent the cover body element to generate the sound.

2. The device according to claim 1, wherein the collecting chamber element and the cover body element are engaged in the first position and are detached from each other in the second position.

3. The device according to claim 2, wherein the gap is sized such that the gap is wider than the amplitude of vibration of the collecting chamber element upon detachment.

4. The device according to claim 1, wherein the collecting chamber element is resiliently deformable whereby the collecting chamber element generates the sound by vibration upon recovery from deformation resulting from engagement and detachment with the cover body element.

5. The device according to claim 4, wherein the collecting chamber element is more resiliently deformable than the cover body element such that the sound is mainly generated by vibration of the collecting chamber element.

6. The device according to claim 4, wherein the cover body element is more resiliently deformable than the collecting chamber element such that the sound is mainly generated by vibration of the cover body element.

7. The device according to claim 1, wherein the sound indicates initiation of an amount of time needed to read analyte test results.

8. The device according to claim 1, wherein the indication structure indicates that the cover body seals the collecting chamber opening upon generation of the sound via transitioning from the first position to the second position.

9. The device according to claim 1, wherein the sample is urine or saliva.

\* \* \* \* \*